United States Patent [19]
Greco et al.

[11] Patent Number: 5,290,516
[45] Date of Patent: Mar. 1, 1994

[54] MOISTURE INDICATOR

[75] Inventors: Mariano Greco, Pittsburgh; Brenda Lesperance, Blawnox; Grace L. Shine, Gibsonia, all of Pa.

[73] Assignee: Bacharach, Inc., Pittsburgh, Pa.

[21] Appl. No.: 965,058

[22] Filed: Oct. 22, 1992

Related U.S. Application Data

[63] Continuation of Ser. No. 488,239, Mar. 5, 1990, abandoned.

[51] Int. Cl.$^5$ .................... G01N 31/22; G01N 33/18
[52] U.S. Cl. ................................. 422/57; 422/59; 436/41; 436/166
[58] Field of Search ............... 436/36, 39, 41, 166; 252/408.1; 422/57, 59

[56] References Cited

U.S. PATENT DOCUMENTS

| | | | |
|---|---|---|---|
| 2,460,065 | 1/1949 | Davis | 252/408 |
| 2,526,938 | 10/1946 | Davis | 436/41 |
| 3,216,802 | 11/1965 | Smith, Jr. | 23/230 |
| 3,861,797 | 5/1972 | Meloan et al, | 252/408 |
| 3,865,537 | 2/1975 | Painter et al. | 431/13 |
| 4,018,061 | 4/1977 | Williamitis | 62/125 |
| 4,923,806 | 5/1990 | Klodowski | 436/39 |

OTHER PUBLICATIONS

Basic Gas Chromatography, Authors: H. M. McNainer, E. J. Bonelli, Copyright Aug. 1968, 4th edition, p. 64, Pan coating method of Column Preparation.
The Practice of Gas Chromatography, Leslie S. Ettre, Albert Zlatkis, 1967, p. 200, Preparation of Packed Columns—Column Material for GLC-Batch Coating.
Modern Practice of Gas Chromatography, Robert L. Grob, 2d edition, p. 146 Evaporation Technique.
Refrigerating Engineering, W. O. Krause, A. B. Guise, 1957, A Simple Moisture Indicating Device for Refrigerating Systems.

*Primary Examiner*—Jill A. Johnston
*Attorney, Agent, or Firm*—Webb, Burden, Ziesenheim & Webb

[57] ABSTRACT

A method and product whereby color changing indicator salts such as cobaltous salts, preferably $CoCl_2$ or $CoBr_2$, are firmly adhered to sand, other particulate silicas or other carriers so that unwanted fines, material loss and solvent washing characteristic of prior indicator salt-coated carriers are eliminated. The process is carried out by thoroughly dehydrating a quantity of cobaltous salts and dissolving and storing the dehydrated cobaltous salt in absolute alcohol, preferably absolute ethanol. The absolute alcohol/cobaltous salt solution is then contacted onto a dehydrated or anhydrous carrier material and the absolute alcohol solvent is removed.

13 Claims, No Drawings

MOISTURE INDICATOR

This is a continuation of copending application Ser. No. 07/488,239 filed on Mar. 5, 1990 and now abandoned.

FIELD OF THE INVENTION

The present invention relates to moisture detection, a capability required in a number of industries including HVAC (heating, ventilating and air conditioning) and other industries in which refrigerants and other moisture sensitive materials are used.

BACKGROUND OF THE INVENTION

Refrigerant-containing systems, such as air conditioning, usually contain a desiccant to prevent moisture accumulation in the refrigerant. If moisture accumulation in the refrigerant is not avoided, valve and control member corrosion leads to inevitable systems malfunctions. As a practical matter, no desiccant has infinite capacity, and as a result it is customary for a visual moisture indicator to be included in a refrigerant-containing system. Ordinarily, visual moisture indication is provided by means of a receptacle which cooperates with an instrument that samples refrigerant from the compressor. Such a receptacle contains a chemical compound or composition which undergoes a color change when it is exposed to moisture.

Although a number of chemical compositions change color in the presence of moisture, particularly well suited chemical salts for moisture indication are cobaltous chloride ($CoCl_2$) and cobaltous bromide ($CoBr_2$). Cobaltous chloride is relatively inexpensive and yet provides distinct, reversible color change upon hydration to $CoCl_2*6H_2O$. Cobaltous chloride is blue in its dry state, but its color rapidly changes to pink (a good "alarm" hue) in the presence of moisture. When hydrated $CoCl_2$ is dried, the $CoCl_2$ turns blue again. $CoBr_2$ anhydrous is green, but turns (reversibly) yellowish salmon pink in the presence of moisture.

As an economic and practical matter, $CoCl_2$ or $CoBr_2$ (or any other color changing moisture indicating composition) is typically adhered to a particulate carrier. The combined cobaltous-salt-coated particulate is then provided, by means of disposable or reusable prepackaged tubes, etc., to the receptacle in the instrument which samples the refrigerant or other moisture sensitive fluid.

SUMMARY OF THE PRIOR ART

U.S. Pat. No. 2,460,065 to Davis discloses a moisture indicator which contains cobaltous chloride (or other indicator salt(s)) with silica gel as the carrier. U.S. Pat. No. 4,018,061 to Williamitis discloses application of a cobaltous salt onto the surface of a hygroscopic plastic cylinder, which cylinder functions as the carrier for the moisture indicating salt. U.S. Pat. No. 3,216,802 to Smith, Jr. discloses the use of cobaltous chloride on paper as a moisture indicator.

In at least some if not all applications, the best carrier is the one which is both effective and inexpensive. An ideal carrier for cobaltous indicator salts is sand, or the particulate silicas generally. It is known to adhere $CoCl_2$ to particulate silica for the purpose of providing color-changing particulates to the appropriate receptacle in a moisture indicator, but prior methods of adhering cobaltous salts to sand particles have met with significant problems. For example, it is known to contact sand with an aqueous solution of cobaltous salt, with subsequent drying of the sand to restore the anhydrous state and blue color of the cobaltous salt. Unfortunately, during the drying process, spalling, fines and cobaltous salt loss occur, and a chloroform wash is ordinarily used to rinse the fines from the coated sand. The spalling, fines and material loss and the use of an organic solvent cleaning step pose economic constraints upon the cost-effective manufacture of cobaltous-salt-coated particulate silica. Any method which avoids the prior art fines and material loss and further avoids the use of an organic solvent represents a significant advance in this moisture indicating technology.

SUMMARY OF THE INVENTION

As such an improved method, the present invention is a method and product whereby cobaltous salts, preferably cobaltous halides, more preferably $CoCl_2$ or $CoBr_2$, are firmly adhered to sand or other particulate silica carriers so that fines, material loss and solvent washing are eliminated. The process is carried out by thoroughly dehydrating a quantity of cobaltous salt and dissolving and storing the dehydrated cobaltous salt in absolute alcohol. The absolute alcohol/cobaltous salt solution is then poured over and mixed with the sand or particulate silica to be coated, under moisture-free conditions. Appropriate quantities are selected to yield the percent cobaltous salt desired on the particle surfaces. The alcohol is evaporated with heat and a coated particulate results in which the cobaltous salt is firmly adhered (that is, does not undergo spalling to any significant degree) to the particulate carrier. No solvent washing step is necessary because the process generates little or no spalling or unwanted fines.

DETAILED DESCRIPTION OF THE INVENTION

The present invention relates to a cobaltous salt-bearing particulate indicator material, which in turn has utility in a wide variety of indicator instruments and applications. The present cobaltous salt/particulate silica combination is therefore not limited to monitoring refrigerant-containing systems, although such is an important application.

Although the following description is directed to cobaltous chloride ($CoCl_2$), other known cobaltous indicator salts including $CoBr_2$ or other cobaltous halides or cobaltous indicator salts may be used. Noncobaltous indicator salts known in the art may also be used. Cobaltous chloride is preferred for use in the present invention because it is relatively inexpensive and provides an appropriate red-family indicator color, pink. Cobaltous bromide is equally preferred in different applications, because although its hydrated salmon-pink color is not as pink as the hydrated $CoCl_2$ appears, the color change still provides a satisfactory indicator and cobaltous bromide is more sensitive to moisture than $CoCl_2$. The $CoBr_2$ embodiment of the invention can be used in applications requiring detection of a lesser water or moisture contamination in place of the embodiment incorporating the cobaltous chloride.

As the first step in adhering $CoCl_2$ to a particulate carrier such as sand, $CoCl_2*6H_2O$ is dehydrated and is dissolved and stored in absolute alcohol to maintain the $CoCl_2$ in its anhydrous condition. The $CoCl_2$/absolute alcohol solution is coated onto the particulate silica and the coated particulate silica is dried. The quantity of $CoCl_2$ per ml. of alcohol may vary depending upon the total weight of the particulate silica to be coated and the percent by weight amount of $CoCl_2$ desired. For example, if 5.0%±0.5% by weight $CoCl_2$ is required to be adhered to 1,000 grams of sand, 50±5 grams of $CoCl_2 \cdot 6H_2O$ is first dried and then dissolved in 200 ml. of absolute alcohol (a volume suitable for thoroughly wetting 1,000 grams of particulate silica). The solution is applied to the sand and is stirred and heated until the alcohol is evaporated. The resulting product is a blue, uniformly coated aggregation of silica particles having firmly adhered thereto 5.0%±0.5% by weight $CoCl_2$.

In the above context, dehydrating a material does not imply that water or moisture was present in the material prior to the dehydration. Dehydration, as a step of the present process, means that a material is subjected to conditions which assure that the material is free or very substantially free of moisture.

The above example wherein 5.0%±0.5% $CoCl_2$ is adhered to particulate sand, based on the weight of the sand, is exemplary. Generally, between about 1 and 12% by weight cobaltous chloride based on the weight of the sand may be adhered to the sand (or other particulate silica or other carrier) in order to obtain a suitable moisture indicator in accordance with the present invention. In other words, 1,000 grams of sand may be contacted with about 10–120 grams $CoCl_2$ in solution. Less than about 1% $CoCl_2$ will yield an indicator in which the color change is difficult to see due to the low concentration of $CoCl_2$. Conversely, greater than about 12% $CoCl_2$ provides not only unnecessary expense but requires a relatively unwieldy amount of absolute alcohol solvent. The preferred percent incorporation of $CoCl_2$ by weight is 5.0%±0.5% $CoCl_2$, which represents adequate $CoCl_2$ for good color change visibility yet moderation of the expense and solubility difficulties presented by higher concentrations of $CoCl_2$.

As a result of the present process, $CoCl_2$ can be adhered to the silica surface faster than with prior art aqueous methods, because the absolute alcohol of the present process evaporates completely and more rapidly than an aqueous solution can evolve. Preparation of the $CoCl_2$-coated particulate silica in this way also produces drastically fewer fines, spalling and material loss than are produced during manufacture with aqueous $CoCl_2$ coating compositions, and the product of the present invention likewise does not generate fines or experience material loss during handling subsequent to manufacture. Accordingly, the present process does not require a chloroform rinse to remove unwanted fines, because it does not generate unwanted fines in the first place.

Cobaltous salts contemplated for use in the present process and product, in addition to $CoCl_2$, include but are not limited to cobaltous sulfate, cobaltous bromide, cobaltous phosphate, cobaltous iodide, cobaltous thiocyanate and cobaltous fluorosilicate. Although for obvious reasons (low cost, low toxicity) absolute ethanol is preferred as the absolute alcohol of the present process, other absolute alcohol carriers may be used including absolute methanol, one or a mixture of the (absolute) propanols or other lower alkyl aliphatic alcohols in their absolute form. In the context of the present invention, "absolute" means free or very substantially free of water. Because an object of the present invention is to eliminate the organic solvent rinse of prior art processes, absolute ethanol is the preferred solvent for the present cobaltous salts.

Sand and other inert particulate silicas known in the art are ordinarily used in sizes of about 30–50 mesh, or 40 mesh preferably. In accordance with the present invention and the applicability of the present moisture indicator material in a number of industries and applications, however, particulate carriers having a particle size between about 10–100 mesh are also contemplated. Nonparticulate carriers may also be used as the base to which a color changing indicator salt is adhered according to the present process.

The indicator material of the present invention is often provided to small, thin tubes, adapted to be opened at each end and receive a gas therein, which are made of glass or other inert transparent material which allows visual inspection of the tube contents. These tubes are known in the art, and are widely used for monitoring refrigerant-containing systems.

EXAMPLE I

Particulate silica was sieved to 30–50 mesh and was stored in an airtight container. Glassware was washed, rinsed thoroughly in deionized water, dried in a convection oven at 75±5° C. for a minimum of two hours and was stored in a clean dry ambient area (closed cabinet). Fifty ± five grams of cobaltous chloride crystals (available from Sargent Welch (Mallinckrodt, Product No. 4532 or equivalent)) were weighed and charged to a 16 ounce wide mouth glass bottle. The open bottle was placed in a 150°–160° C. oven overnight (12 hours minimum), after which the cobaltous chloride appeared powder blue. The bottle was removed from the oven and was immediately tightly covered and allowed to cool to room temperature. The dehydrated cobaltous chloride was then stored for several days.

Prior to coating of the particulate silica, 200 ml. of absolute ethanol was charged to the bottle containing the dehydrated and cooled cobaltous chloride and the lid was replaced immediately. Over a period of a little over 24 hours, with occasional shaking, the cobaltous chloride dissolved into the absolute ethanol.

An 8"×8"×2" Pyrex ® (heat tempered glass) baking dish was tared, and into it was weighed 1,000 grams ±10 grams of the previously-sieved 30–50 mesh sand. All of the cobaltous chloride solution in absolute ethanol was poured over the sand in the dish with thorough mixing with a stainless steel spoon, and after the stirring all the sand was completely wetted and covered with the solution. The dish with the wetted sand was placed on a hot plate on "low" (to achieve a 90°–100° C. sand temperature) and the sand was stirred constantly until all the alcohol evaporated. An infra-red lamp was directed toward the sand to facilitate drying. The color of the sand changed from a dark blue when wet to a light blue with some pink, during and after alcohol evaporation.

The dried sand was stirred gently and was transferred to a second 8"×8"×2" Pyrex ® (heat tempered glass) dish. A small amount of caked sand remaining in the first Pyrex ® (heat tempered glass) dish was discarded. The hot plate was turned to a medium high temperature setting (to achieve a 200°–250° C. sand temperature) with continued gentle stirring until the cobaltous chloride-coated sand achieved a powder blue color.

A 20 mesh sieve was stacked onto a 70 mesh sieve. The cobaltous chloride-coated silica was charged, while it was still hot, to and through the sieves. The sand remaining in the 20 mesh sieve was discarded, and the sand remaining in the 70 mesh sieve was bottled as follows.

A bottle for storing the cobaltous chloride-coated sand was purged with nitrogen for 30 seconds. The hot sand remaining in the 70 mesh sieve was immediately poured through a grounded (to eliminate static cling) stainless steel funnel into the storage bottle, leaving 0.5" headroom. The bottle was tightly capped and sealed with electrical tape. The bottle was stored in a closed cabinet until its contents were charged to small tubes known in the art for moisture indicating applications.

EXAMPLE II

The process according to Example I was repeated with particulate silica of the same particle size being prepared in identical fashion, except $50\pm5$ grams of cobaltous bromide ($CoBr_2$) were substituted for the $50\pm5$ grams of cobaltous chloride.

The indicator salt/sand combination demonstrated greater sensitivity to water and shorter reaction time in the presence of water than the indicator material prepared according to Example I. The pink color which resulted upon hydration of the $CoBr_2$ was of a more yellow/orange hue than the pink color which is obtained from the hydration of $CoCl_2$, but still provided an appropriate red-family indicator color. Test results support the conclusion that the rate of color change for cobaltous bromide is approximately ten times faster than the rate for cobalt chloride.

Although the invention has been described with respect to particular materials and processes described above, the invention is only to be limited insofar as is set forth in the accompanying claims.

We claim:

1. A process for preparing a moisture indicator material, comprising the steps of dehydrating a carrier material comprising 10–100 mesh sand, dehydrating a quantity of a cobaltous indicator composition which changes color upon exposure to moisture, dissolving said cobaltous indicator composition in an absolute alcohol solvent, contacting said carrier material with said dissolved cobaltous indicator composition and removing said absolute alcohol solvent, wherein spalling of said cobaltous indicator composition from said carrier material is drastically reduced compared to moisture indicator materials in which the carrier is not preliminarily dehydrated and in which the solvent is not absolute.

2. The process according to claim 1 wherein said cobaltous indicator composition further comprises a composition selected from the group consisting of cobaltous chloride and cobaltous bromide wherein said cobaltous indicator composition is dehydrated at 150°–160° C. for a minimum of twelve hours.

3. The process according to claim 2 wherein said indicator composition further comprises cobaltous chloride, and about 10–120 grams of said cobaltous chloride is dissolved in said absolute alcohol solvent and is subsequently contacted with about 1,000 grams of said carrier, prior to removal of said absolute alcohol solvent.

4. The process according to claim 3 wherein said absolute alcohol solvent is absolute ethanol.

5. The process according to claim 4 wherein said sand has a particle size between 30 and 50 mesh.

6. The process according to claim 4 wherein said cobaltous chloride is dissolved in said absolute ethanol over a period exceeding 24 hours.

7. The process according to claim 3 wherein said absolute alcohol solvent is removed by heating and stirring said sand.

8. The process according to claim 7 wherein after said absolute alcohol solvent is removed from said sand, a cobaltous chloride-coated sand indicator material is charged to a tube for use in detecting moisture.

9. The process according to claim 3 wherein $50.0\pm0.5$ grams cobaltous chloride is dissolved and contacted with about 1,000 grams sand.

10. The process according to claim 9 wherein said sand has a particle size of 40 mesh.

11. The process according to claim 1 wherein said cobaltous indicator composition is cobaltous bromide, and wherein said absolute alcohol solvent is removed by heating said carrier.

12. The process according to claim 1 wherein said cobaltous indicator composition is selected from the group consisting of cobaltous bromide, cobaltous sulfate, cobaltous thiocyanate, cobaltous fluorosilicate, cobaltous phosphate and cobaltous iodide.

13. The product prepared according to the process of any one of claims 1–5 and 7–12.

* * * * *